United States Patent [19]

Melloni et al.

[11] Patent Number: 4,624,949
[45] Date of Patent: Nov. 25, 1986

[54] DIBENZO[B,D]THIOPYRAN DERIVATIVES, PHARMACEUTICAL COMPOSITION AND USE

[75] Inventors: Piero Melloni, Bresso; Paolo Salvadori; Pier P. Lovisolo, both of Milan, all of Italy

[73] Assignee: Farmitalia Carlo Erba, S.p.A., Milan, Italy

[21] Appl. No.: 835,946

[22] Filed: Mar. 4, 1986

[30] Foreign Application Priority Data

Mar. 6, 1985 [GB] United Kingdom ............... 8505756

[51] Int. Cl.[4] .................. A61K 31/38; A61K 31/535; C07D 35/10; C07D 413/12
[52] U.S. Cl. ............................ 514/222; 514/231; 514/252; 514/324; 514/422; 514/437; 544/58.4; 544/58.7; 544/145; 544/364; 544/375; 546/202; 548/525; 549/26
[58] Field of Search .............. 544/58.4, 58.7, 145, 544/364, 375; 546/202; 548/525; 549/26; 514/222, 231, 252, 324, 422, 437

[56] References Cited

U.S. PATENT DOCUMENTS 3,723,465   3/1978   Hall et al. ......................... 549/26

OTHER PUBLICATIONS

U.S. Pat. No. 3,944,673 (Farmdoc 24298X) Eli Lilly Co.
Belgian Pat. No. 823,873 (Farmdoc 34237W) Farmitalia Carlo Erba Spa.
Belgian Pat. No. 890,773 (Farmdoc 35242E) Farmitalia Carlo Erba SpA.
U.S. Pat. No. 4,166,062 (Farmdoc 67882B) Upjohn Co.
U.S. Pat. No. 4,179,510 (Farmdoc 01677C) Upjohn Co.
Belgian Pat. No. 871,702 (Farmdoc 33369B) Upjohn Co.
Aust. J. Chem. 1983, 36(4), 795-802 (Chemical Abstracts 99:13970w).
J. Chem. Soc. Perkin Trans 1, 1982, (4), 91722 (Chemical Abstracts 97:55648a).
Japan Kokai JJ 1138-680 (Farmdoc 04559Y) Grelan Pharmaceutical KK.
Japan Kokai J5 2105-174 (Farmdoc 73604Y) Grelan Pharmaceutical KK.
Japan Kokai J5 5149-300 (Farmdoc 04916D) Grelan Pharmaceutical KK.

Primary Examiner—Robert W. Ramsuer
Attorney, Agent, or Firm—Murray and Whisenhunt

[57] ABSTRACT

The invention relates to compounds having the general formula (I)

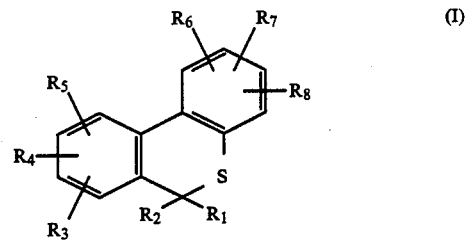

wherein
$R_1$ is carboxy, esterified carboxy or an amide of formula

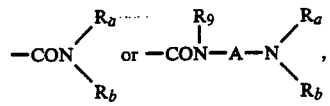

in which $R_9$ is hydrogen or $C_1$–$C_6$ alkyl, A is $C_2$–$C_6$ alkylene and $R_a$ and $R_b$ are hydrogen or $C_1$–$C_6$ alkyl or $R_a$ and $R_b$ taken together with the nitrogen atom to which they are linked form a saturated, optionally substituted, heteromonocyclic ring;
$R_2$ is hydrogen or $C_1$–$C_6$ alkyl;
each of $R_3$ to $R_8$ is independently hydrogen, halogen, $C_1$–$C_6$-alkyl, $C_3$–$C_4$ alkenyloxy or $C_1$–$C_6$ alkoxy; and the pharmaceutically acceptable salts thereof, which are useful as immunomodulating and antiviral agents.

10 Claims, No Drawings

DIBENZO[B,D]THIOPYRAN DERIVATIVES, PHARMACEUTICAL COMPOSITION AND USE

The present invention relates to new tricyclic dibenzo condensed derivatives, in particular to new 6-substituted 6H-dibenzo [b,d]thiopyran derivatives, to a process for their preparation and pharmaceutical compositions containing them.

The compounds of the invention have the general formula (I)

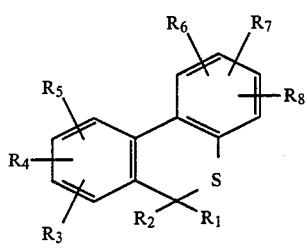

wherein
$R_1$ represents
(a) carboxy;
(b) esterified carboxy;
(c) a

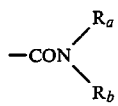

group, wherein each of $R_a$ and $R_b$, being the same or different, is hydrogen or $C_1$-$C_6$ alkyl, or $R_a$ and $R_b$, taken together with the nitrogen atom to which they are linked, form a saturated heteromonocyclic ring, optionally containing a further heteroatom chosen from oxygen, sulphur and nitrogen, wherein the additional nitrogen atom may be unsubstituted or substituted by $C_1$-$C_6$ alkyl, pyridyl or by phenyl; or
(d) a

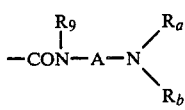

group, wherein $R_9$ is hydrogen or $C_1$-$C_6$ alkyl, A is a $C_2$-$C_6$ alkylene chain and $R_a$ and $R_b$ are as defined above;
$R_2$ represents hydrogen or $C_1$-$C_6$ alkyl;
each of $R_3$, $R_4$, $R_5$, $R_6$, $R_7$ and $R_8$, which may be the same or different, is hydrogen, halogen, $C_1$-$C_6$ alkyl, $C_3$-$C_4$-alkenyloxy or $C_1$-$C_6$ alkoxy; and the pharmaceutically acceptable salts thereof.

The invention also includes within its scope all the possible isomers, stereoisomers and optical isomers and their mixtures, and the metabolites and the metabolic precursors or bio-precursors of the compounds of formula (I).

A halogen atom is preferably chlorine or bromine.

The alkyl, alkylene, alkenyloxy and alkoxy groups may be branched or straight chain groups.

A $C_1$-$C_6$ alkyl group is e.g. methyl, ethyl, propyl, isopropyl, butyl, sec-butyl or tert.butyl, preferably methyl or ethyl.

A $C_3$-$C_4$ alkenyloxy group is preferably allyloxy.

A $C_1$-$C_6$ alkoxy group is e.g. methoxy, ethoxy, propoxy, isopropoxy, butoxy or ter.butoxy, preferably it is methoxy, ethoxy or propoxy.

The alkylene chain A is preferably a $C_2$-$C_4$ alkylene chain. When $R_a$ and $R_b$, taken together with the nitrogen atom to which they are linked, form a saturated heteromonocyclic ring, this may be for example a saturated, 5- or 6-membered heteromonocyclic ring chosen from the group including pyrrolidine, piperidine, piperazine, morpholine and thiomorpholine; when the heteromonocyclic ring is piperazine, it may be unsubstituted or substituted as defined above; preferably it is substituted by $C_1$-$C_4$ alkyl, pyridyl or by phenyl.

When $R_1$ is an esterified carboxy group, it is preferably a —$COXR_{10}$ group, wherein X is —O— or —S— and $R_{10}$ is $C_1$-$C_6$ alkyl unsubstituted or substituted by

wherein $R_a$ and $R_b$ are as defined above; more preferably it is a —$COXR'_{10}$ group, wherein X is as defined above and $R'_{10}$ is a $C_1$-$C_4$ alkyl group unsubstituted or substituted by a

group, wherein each of $R'_a$ and $R'_b$ is independently hydrogen or $C_1$-$C_4$ alkyl, or $R'_a$ and $R'_b$, taken together with the nitrogen atom to which they are linked, form a pyrrolidine, piperidine, morpholine, thiomorpholine or piperazine ring, wherein the piperazine ring may be unsubstituted or substituted by $C_1$-$C_4$ alkyl, pyridyl or by phenyl.

A particularly preferred value of $R_1$ as esterified carboxy group is

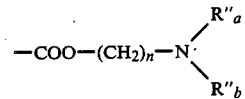

wherein n is 2 or 3, each of $R''_a$ and $R''_b$ is independently $C_1$-$C_4$ alkyl or $R''_a$ and $R''_b$ taken together with the nitrogen atom to which they are linked form a pyrrolidine, morpholine or piperidine ring. A pyridyl group may be a 2-, 3- or 4-pyridyl ring, preferably it is a 2-pyridyl ring.

The pharmaceutically acceptable salts of the compounds of formula (I) include those formed with an inorganic acid, e.g. hydrochloric acid or sulphuric acid, or with an organic acid, e.g. citric, tartaric, malic, maleic, mandelic, fumaric or methanesulphonic acid, or with an inorganic base, e.g. sodium, potassium, calcium or aluminium hydroxide or an alkali metal or alkaline earth metal carbonate or bicarbonate, or with an organic base, typically an organic amine, e.g. lysine, triethylamine, procaine, dibenzylamine, N-benzyl-β- phenethylamine, N,N'-dibenzyl-ethylenediamine, dehydroabietylamine, N-ethyl-piperidine, diethanolamine, N-methyl-glucamine, or tris-hydroxymethyl-aminomethane. As stated above the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are compounds of formula (I), wherein:

$R_1$ represents (a') an esterified carboxy group of formula $-COXR'_{10}$, wherein X is $-O-$ or $-S-$ and $R'_{10}$ is $C_1-C_4$ alkyl unsubstituted or substituted by a

group, wherein each of $R'_a$ and $R'_b$ is independently hydrogen or $C_1-C_4$ alkyl, or $R'_a$ and $R'_b$, taken together with the nitrogen atom to which they are linked, form a pyrrolidine, piperidine, morpholine, thiomorpholine or piperazine ring, wherein the piperazine ring may be unsubstituted or substituted by $C_1-C_4$ alkyl, pyridyl or by phenyl; or (b') a

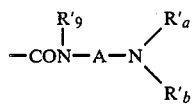

group, wherein $R'_9$ is hydrogen or $C_1-C_4$ alkyl and A, $R'_a$ and $R'_b$ are as defined above;

$R_2$ is hydrogen or $C_1-C_4$ alkyl;

each of $R_3$, $R_4$, $R_5$, $R_6$, $R_7$ and $R_8$ is independently hydrogen, chlorine, bromine, $C_1-C_4$ alkyl or $C_1-C_4$ alkoxy; and the pharmaceutically acceptable salts thereof.

Particularly preferred compounds of the invention are the compounds of formula (I), wherein $R_1$ represents (a'') a $C_1-C_4$ alkoxy-carbonyl group;

(b'')

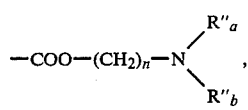

wherein n is 2 or 3, each of $R''_a$ and $R''_b$ is independently $C_1-C_4$ alkyl or $R''_A$ and $R''_B$ taken together with the nitrogen atom to which they are linked form a pyrrolidine, morpholine or piperidine ring;

(c'')

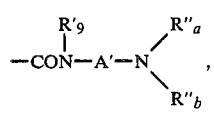

wherein $R'_9$ is hydrogen or $C_1-C_4$-alkyl, A' is a $C_2-C_4$ alkenylene chain and $R''_a$ and $R''_b$ are as defined above;

$R_2$ is hydrogen;

each of $R_3$, $R_4$, $R_5$, $R_6$, $R_7$ and $R_8$ is independently hydrogen, chlorine, $C_1-C_4$ alkyl or $C_1-C_4$ alkoxy; and the pharmaceutically acceptable salts thereof.

More preferred compounds of the invention are the compounds of formula (I) wherein $R_1$ is (a''') $C_1-C_4$ alkoxy-carbonyl;

(b''')

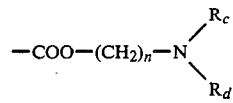

wherein n is 2 or 3 and each of $R_c$ and $R_d$ is independently $C_1-C_4$ alkyl; or (c''')

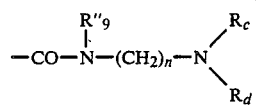

wherein $R''_9$ is $C_1-C_4$ alkyl and $R_c$, $R_d$ and n are as defined above;

$R_2$ is hydrogen;

each of $R_3$, $R_4$, $R_5$, $R_6$, $R_7$ and $R_8$ is hydrogen; and the pharmaceutically acceptable salts thereof.

Specific examples of compounds of the invention are the following:

6H-dibenzo [b,d]thiopyran-6-carboxylic acid;

6H-dibenzo [b,d]thiopyran-6-carboxylic acid, 2-N,N-dimethylamino-ethyl ester;

6H-dibenzo[b,d]thiopyran-6-carboxylic acid, 2-N,N-dimethyl-amino-ethylthio 6H-dibenzo[b,d]thiopyran-6-carboxylic acid, 3-N,N-dimethylamino-propyl ester;

6H-dibenzo[b,d]thiopyran-6-carboxylic acid, 2-N,N-diethylamino-ethyl ester;

6H-dibenzo[b,d]thiopyran-6-carboxylic acid, 2-morpholino-ethyl ester;

6H-dibenzo[b,d]thiopyran-6-carboxylic acid, 2-(pyrrolidin-1-yl)-ethyl ester;

6H-dibenzo[b,d]thiopyran-6-N-(2-N,N-dimethylamino-ethyl)-carboxamide;

6H-dibenzo[b,d]thiopyran-6-N-methyl-N-(2-N,N-dimethylamino-ethyl)-carboxamide;

6H-dibenzo[b,d]thiopyran-6-N-(3-N,N-dimethylamino-propyl)-carboxamide;

6-(4-methyl-piperazin-1-yl)-carbonyl-6H-dibenzo[b,d]thiopyran;

6-[4-(2-pyridyl)-piperazin-1-yl]-carbonyl-6H-dibenzo[b,d]thiopyran;

and the pharmaceutically acceptable salts thereof.

The compounds of the invention and the salts thereof can be prepared by a process comprising:

(A) reacting a compound of formula (II)

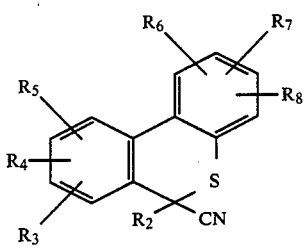

(II)

wherein $R_2$, $R_3$, $R_4$, $R_5$, $R_6$, $R_7$ and $R_8$ are as defined above, with a $C_1$-$C_6$ alkyl alcohol or a $C_1$-$C_6$ alkylthiol, so obtaining a compound of formula (I), wherein $R_1$ is $C_1$-$C_6$ alkoxycarbonyl or $C_1$-$C_6$ alkylthio-carbonyl, and (i) if desired, converting a compound of formula (I), thus obtained into another compound of formula (I), wherein $R_1$ is a free carboxy group, and, (ii) if desired, converting the carboxylic acid or formula (I) thus obtained into another compound of formula (I) wherein $R_1$ is as defined in formula (I) under (b), (c) or (d) but is not $C_1$-$C_6$ alkoxy-carbonyl or $C_1$-$C_6$ alkylthio-carbonyl; or (B) hydrolyzing a compound of formula (II), as defined above, so obtaining, depending on the reaction conditions a compound of formula (I), wherein $R_1$ is either carbamoyl or a free carboxy group, and, (iii) if desired, converting a so obtained compound of formula (I), wherein $R_1$ is a free carboxy group, into another compound of formula (I), wherein $R_1$ is as defined in formula (I) under (b), (c) or (d);

and/or, if desired, converting a compound of formula (I) into another compound of formula (I), and/or, if desired, converting a compound of formula (I) into a pharmaceutically acceptable salt thereof, and/or, if desired, converting a salt of a compound of formula (I) into a free compound, and/or, if desired, separating a mixture of isomers of compounds of formula (I), into the single isomers. The reaction of a compound of formula (II) with a $C_1$-$C_6$-alkyl alcohol or a $C_1$-$C_6$ alkylthiol may be carried out in a conventional way, for example in the presence of an acid catalyst, preferably a mineral acid, such as $H_2SO_4$, HCl or HBr, at a temperature ranging from about 30° C. to the reflux temperature.

The hydrolysis of a compound of formula (II) to afford a compound of formula (I), wherein $R_1$ represents carbamoyl may be carried out according to well known methods, for example, by treatment with 85% $H_2SO_4$ at a temperature varying between about 50° C. and about 100° C. or by heating with water in the presence of copper powder as catalyst under inert atmosphere at a temperature varying from about 60° C. to about 100° C.

Also the hydrolysis of a compound of formula (II) to afford a compound of formula (I), wherein $R_1$ represents a free carboxy group, may be carried out according to known procedures, for example by treatment with a basic agent, preferably aqueous NaOH or KOH, in a suitable solvent, e.g. water, dioxane, lower aliphatic alcohols e.g. $C_1$-$C_4$ alkyl alcohols, or their mixtures, at a temperature of from about 30° C. to the reflux temperature, followed by acidification.

The optional steps (i), (ii) and (iii) described above may be carried out according to known procedures.

For example, the optional step regarding the conversion of a compound of formula (I), wherein $R_1$ is $C_1$-$C_6$ alkoxy-carbonyl or $C_1$-$C_6$ alkylthio-carbonyl, obtained according to process (A), into another compound of formula (I), wherein $R_1$ is a free carboxy group, may be a basic hydrolysis, carried out by using e.g. sodium or potassium hydroxide, in a solvent, such as, e.g., water or a lower aliphatic alcohol, and operating at a temperature ranging from the room temperature to about 150° C. and then acidifying; or an acid hydrolysis, for example, in a solvent, such as, water, or mixtures of aliphatic alcohol or dioxane with water, operating at a temperature ranging from the room temperature to the reflux temperature; the same reaction may be also carried out e.g. by treatment with a lithium halide, preferably lithium bromide in a suitable solvent, e.g. dimethylsulphoxide, hexamethylphosphorotriamide or dimethylformamide, preferably in dimethylformamide at a temperature higher than 50° C.

The optional step concerning the conversion of a carboxylic acid of formula (I) into another compound of formula (I), wherein $R_1$ represents an esterified carboxy group, may be carried out according to well known methods, for example, said carboxylic acid may be converted into a compound of formula (I) wherein $R_1$ is the group —$COXR_{10}$, wherein $R_{10}$ and X are as defined above, by reacting the alkali metal salt of the acid with an alkyl halide, in an inert solvent, such as, e.g. acetone, dioxane, dimethylformamide or hexamethylphosphorotriamide at a temperature ranging from about 0° C. to about 100° C., or by reacting the acid with a compound of formula $R_{10}$—XH wherein $R_{10}$ and X are as defined above, in the presence of a suitable acid catalyst, e.g. HCl.

Alternatively the same esterification may be effected (a) by converting the carboxylic acid into the corresponding halocarbonyl, preferably chlorocarbonyl, derivative, by reaction, e.g. with the desired acid halide, for example oxalyl chloride, thionyl chloride, $PCl_3$, $PCl_5$ or $POCl_3$, either in the absence of a solvent or in an inert organic solvent, e.g. benzene, toluene, xylene, dioxane, dichloroethane, methylene chloride, or tetrahydrofuran, at a temperature preferably from about 0° C. to about 120° C.; and then (b) reacting the obtained halocarbonyl derivative with the suitable compound of formula $R_{10}$—XH,- wherein $R_{10}$ and X are as defined above, in a solvent which may be the same alcohol or in an inert solvent, e.g. benzene, toluene, xylene, dioxane, dichloroethane, methylene chloride, or tetrahydrofuran, at a temperature preferably from about 0° C. to about 60° C., if desired in the presence of a base, e.g. triethylamine.

The optional step regarding the conversion of a carboxylic acid of formula (I) into another compound of formula (I), wherein $R_1$ represents a —$CONR_aR_b$ or —$CON(R_9)$—A—$NR_aR_b$ group, wherein $R_a$, $R_b$, $R_9$ and A are as defined above, may be carried out according to well known methods too.

For example, by reacting a reactive derivative of such carboxylic acid, e.g. an acyl halide, preferably chloride, or a mixed anhydride, with an amine of formula $HNR_aR_b$ or $HN(R_9)$—A—$NR_aR_b$, wherein A, $R_a$, $R_b$ and $R_9$ are as defined above, respectively.

The reaction may be performed in an organic solvent, such as dioxane, tetrahydrofuran, dichloromethane, chloroform or benzene, at a temperature ranging from about 0° C. to about 100° C., if desired in the presence of a suitable basic agent, e.g. triethylamine.

A compound of formula (I) may be converted into another compound of formula (I) according to known methods;

for example a compound of formula (I), wherein one or more of $R_3$, $R_4$, $R_5$, $R_6$, $R_7$ and $R_8$ are hydrogen may be converted into the corresponding compound of formula (I), wherein one or more of $R_3$, $R_4$, $R_5$, $R_6$, $R_7$ and $R_8$ are halogen by halogenation. In particular, for example, a compound of formula (I) wherein one or more of $R_3$, $R_4$, $R_5$, $R_6$, $R_7$ and $R_8$ are hydrogen may be transformed into a compound of formula (I) wherein one or more of $R_3$, $R_4$, $R_5$, $R_6$, $R_7$ and $R_8$ are chlorine by reaction with a suitable chlorinating agent, for instance with $SO_2Cl_2$ in an organic solvent, e.g. $CH_2Cl_2$ or $CHCl_3$, or by following other well known methods, for example those described in J.O.C., 1970, 35, 719 or Synthesis 1979, 417.

Examples of optional conversion of a compound of formula (I) into another compound of formula (I), are also those described above as optional step (i), (ii) and (iii).

Also the optional salification of a compound of formula (I) as well as the conversion of a salt into the free compounds and the separation of a mixture of isomers into the single isomers may be carried out by conventional methods.

For example the separation of optical isomers may be carried out by salification with an optically active base or acid and by subsequent fractional crystallization of the diastereoisomeric salts followed by recovering of the optically active isomeric acids or, respectively, bases.

The compounds of formula (II), wherein $R_2$ is hydrogen, may be prepared, for example, by reacting a compound of formula (III)

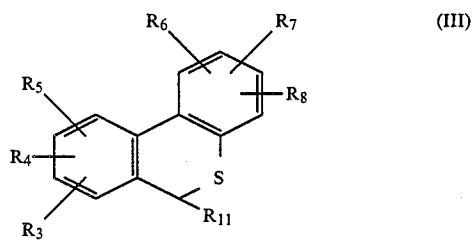

wherein $R_3$, $R_4$, $R_5$, $R_6$, $R_7$ and $R_8$ are as defined above and $R_{11}$ is a halogen atom or a hydroxy group, with an alkali metal cyanide or with a tri($C_1$–$C_6$)-alkylsilylcyanide, preferably trimethylsilylcyanide, respectively.

The reaction of a compound of formula (III) wherein $R_{11}$ is halogen with an alkali metal cyanide may be carried out in a suitable organic solvent, e.g. dimethylformamide, dimethylacetamide, dioxane or, preferably, in an aqueous solvent, e.g. a mixture of dimethylformamide or dimethylacetamide and water, at temperatures ranging from about 0° C. to the solvent reflux temperature, preferably at room temperature.

The reaction of a compound of formula (III) wherein $R_{11}$ is hydroxy with a tri($C_1$–$C_6$)-alkylsilylcyanide may be carried out, for example, in an inert solvent, such as benzene or toluene, in the presence of a suitable catalyst, for example $ZnI_2$, at a temperature ranging from about 0° C. to about 50° C. The compounds of formula (II), wherein $R_2$ is $C_1$–$C_6$ alkyl, may be prepared, for example, by reacting a compound of formula (II), wherein $R_2$ is hydrogen, with a $C_1$–$C_6$ alkyl halide, preferably iodide, in the presence of NaH or a similar strong base, in a suitable anhydrous solvent, such as dimethylformamide, dioxane, toluene, dimethylsulfoxide, at a temperature ranging between about room temperature and about 100° C. The compounds of formula (III) wherein $R_{11}$ is hydroxy may be prepared, for example, by reacting a compound of formula (IV)

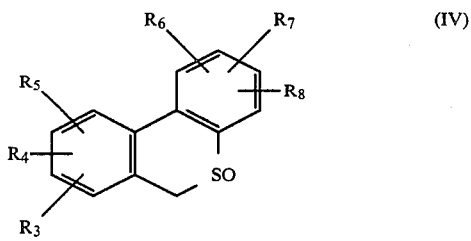

wherein $R_3$, $R_4$, $R_5$, $R_6$, $R_7$ and $R_8$ are as defined above, with trifluoroacetic anhydride in the presence of 2,6-lutidine, in an inert solvent, such as acetonitrile, at a temperature of about 0° C. and then hydrolyzing the trifluoroacetoxy derivative so obtained, by treatment with aqueous sodium bicarbonate at room temperature.

A compound of formula (III) wherein $R_{11}$ is halogen, may be obtained from a compound of formula (III) wherein $R_{11}$ is hydroxy, by treatment with an appropriate halogenating agent, for example by treatment with $SOCl_2$ or $PBr_3$ at temperatures ranging from 0° to 60° C., preferably at room temperature.

The compound of formula (IV) may be obtained by methods of synthesis well known in the art.

When in the new compounds of the present invention and in the intermediate-products thereof, groups are present, which need to be protected before submitting them to the hereabove illustrated reactions, they may be protected before the reactions take place and then deprotected, according to well known methods in organic chemistry.

The compounds of this invention possess immunomodulating activity and in particular antiviral activity.

Their immunomodulating activity is, for example, proven by their capacity to modify the antibody response induced in mice by a suboptimal dose of sheep red blood cells (SRBC) injected by intraperitoneal route (i.p.).

Groups of ten female CD-1 mice were injected i.p. with $2 \times 10^6$ SRBC as antigen. The tested compounds were administered i.p. at two dosage levels: 50 and 5 mg/kg body weight, two hours before the administration of the antigen. A control groups of mice received SRBC and saline instead of the compounds. Six days later the mice were killed and antibody titres against SRBC determined in their sera, according to Williams C. A.: Methods in Immunology and Immunochemistry, C. A. Williams and M. W. Chase, Eds. Academic Press, New York, Vol. 11, page 152, 1977.

The antiviral activity of the compound of the invention was, for example, evaluated against influenza in mice. Groups of CD-1 mice were infected intranasally with the strain APR 8 of influenza virus. The tested compounds were administered through various routes, e.g. intraperitoneally, subcutaneously or orally.

The effect of the tested compounds, against the influenza virus, was evaluated on the basis of the number of lung lesions in the drug-treated animals and in the control group. As preferred example of compound having immunomodulating and antiviral activity the following can be mentioned: 6H-dibenzo [b,d]thiopyran-6-carboxylic acid, 2-N,N-dimethyl-aminoethyl ester (internal code FCE 23101).

The compound FCE 23101 was found active, for example, in increasing the haemolytic antibody production and in protecting the mice from the viral infection induced by APR 8 influenza virus.

Compound FCE 23101 surprisingly was found more active than the chemically related prior art compound 6H-dibenzo[b,d]pyran-6-carboxylic acid, 2-N,N-dimethylaminoethyl ester (internal code FCE 20696), disclosed by U.S. Pat. No. 4,463,001, for example as antiviral agent. In fact compound FCE 23101, e.g. after oral administration, unexpectedly provides the same inhibiting activity against the viral infection induced by APR8 influenza virus in mice, at a dosage which is about one fifth of that required when compound FCE 20696 is administered by the same route.

In view of their high therapeutic index the compounds of the invention can be safely used in medicine.

For example, the approximate acute toxicity ($LD_{50}$) of the compound FCE 23101 in the mouse determined with single administration of increasing doses and measured on the seventh day after the day of treatment is per os higher than 400 mg/kg.

Analogous toxicity data have been found for the other compounds of the invention.

The compounds of formula (I) are useful in the therapy of transplant reactions, for example transplants of kidneys; heart, bone marrow, skin and endocrine glands.

Other areas of pathology, in which the immunomodulating properties of these compounds are of therapeutic benefit: the therapy of neoplastic diseases, acute and chronic infections of both bacterial and viral origin, and of diseases characterized by an immunologic imbalance, like primary or acquired immunodeficiencies and autoimmune disorders. This last category includes rheumatoid arthritis, systemic lupus erythematosus, glomerulonephritis, vasculitis and blood dyscrasias. The therapeutic regimen for the different clinical syndromes must be adapted to the type of pathology.

In transplantation and infections diseases the time of onset and the clinical course are, as a rule, known; conversely, the onset of immunological disorders is unknown and their clinical course is generally long and complex. Hence the therapeutic dose must be determined for each single clinical case, taking into account also the fact that it depends also on the route of administration.

The oral route is employed, in general, for all conditions requiring such compounds. Preference is given to the parenteral route, e.g. intravenous injection or infusion, for the prevention of rejection and the treatment of acute infections. For maintenance regimens the oral or parenteral, e.g. intramuscular or subcutaneous, route is preferred. For these purposes the compounds of the invention can be administered orally at doses ranging e.g. from about 0.5 to about 10 mg/kg of body weight per day.

Doses of active compounds ranging e.g. from about 0.2 to about 5 mg/kg of body weight can be used for the parenteral administration. Of course, these dosage regimens may be adjusted to provide the optimal therapeutic response.

The invention includes a pharmaceutical composition comprising a compound of the invention in association with a pharmaceutically acceptable excipient (which can be a carrier or diluent).

The pharmaceutical compositions of the invention are usually prepared following conventional methods and are administered in a pharmaceutically suitable form, for example the solid oral forms may contain, together with the active compound, diluents, e.g., lactose, dextrose, saccharose, cellulose, corn starch and potato starch, lubricants e.g. silica, talc, stearic acid, magnesium or calcium stearate, and/or polyethylene glycols binding agents, e.g. starches, arabic gums, gelatin, methylcellulose, carboxymethyl cellulose, polyvinyl pyrrolidone, disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carrier only products not metabolizable to glucose, or metabolizable in very small amount to glucose, such as sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

To a stirred solution of 2-benzylthio-aniline (2.4 g ; 0.011 mol) in 70 ml of CH $C_2L_2$ a solution of 85% m.chloroperoxybenzoic acid (2.4 g; 0.012 mol) in 50 ml of $CH_2Cl_2$ was slowly added at 0° C. After 2 hours the mixture was allowed to warm to room temperature and washed with sodium thiosulfate solution, 10% sodium carbonate solution, then dried and concentrated under reduced pressure. The residue was treated with n.pentane; benzyl-(2-aminophenyl)-sulfoxide was filtered as a white solid: (2.1 g; yield 80%); m.p. 90°–94° C.

By proceeding analogously the following compounds were obtained:
benzyl-(2-amino-4-chlorophenyl)-sulfoxide;
benzyl-(2-amino-3,4-dimethoxyphenyl)-sulfoxide, and
benzyl-(2-amino-4-methyl-phenyl)-sulfoxide.

EXAMPLE 2

To a stirred suspension of benzyl-(2-aminophenyl)-sulfoxide (1.9 g; 0.008 mol) in 30 ml of 11% $H_2SO_4$ was added a solution of sodium nitrite (0.78 g; 0.011 mol) in 20 ml of water at about 0° C. After 1 hour at 0° C. to the yellow solution was quickly added a solution of cupric nitrate trihydrate (34.2 g; 0.140 mol) in 75 ml of water and cuprous oxide (1.33 g; 0.009 mol). The solution was allowed to warm to room temperature and stirred for further 5 hours. The solid was filtered and treated with hot ethyl acetate. The solution was dried over sodium sulfate concentrated and the residue was crystallized from ethyl acetate/pentane (1:4) to give 6H-dibenzo[b,d]thiopyran-5-oxide (1.25 g; yield 71%); m.p. 97°–100° C. By proceeding analogously the following compounds were obtained:

1,2-dimethoxy-6H-dibenzo[b,d]thiopyran-5-oxide;
2-chloro-6H-dibenzo[b,d]thiopyran-5-oxide; and
2-methyl-6H-dibenzo[b,d]thiopyran-5-oxide.

EXAMPLE 3

To a stirred solution of 6H-dibenzo[b,d]thiopyran-5-oxide (2 g; 0.0093 mol), 2,6-lutidine (4 ml; 0.034 mol) and acetonitrile (40 ml) was added a solution of trifluoro acetic anhydride (3.2 ml; 0.022 mol) in acetonitrile (10 ml) at 0° C. After 2 hours a solution of $NaHCO_3$ (1 g) in water (25 ml) was quickly added at 0° C. and then the mixture was allowed to warm to room temperature. After 2 hours the mixture was poured into water (200 ml) and extracted with diethyl ether. The extracts were dried, concentrated and separated on silica gel chromatography column (ethyl acetate:cyclohexane 1:4 as eluant) to give 6H-dibenzo[b,d]thiopyran-6-ol; (1.2 g; yield 60%); m.p. 83°–86° C. By proceeding analogously the following compounds were obtained:

1,2-dimethoxy-6H-dibenzo[b,d]thiopyran-6-ol;
2-chloro-6H-dibenzo[b,d]thiopyran-6-ol; and
2-methyl-6H-dibenzo[b,d]thiopyran-6-ol.

EXAMPLE 4

6H-dibenzo[b,d]thiopyran-6-ol (2.6 g; 12 mmol) was dissolved in anhydrous benzene (50 ml). Trimethylsilyl-cyanide (4.5 ml; 36 mmol) and a catalytic amount of $ZnI_2$ were added to the solution, then the reaction mixture was stirred for 20 hours at room temperature. The solution was washed with 1N NaOH, dried and evaporated. The residue was crystallized from diethyl ether to give 6-cyano-6H-dibenzo[b,d]thiopyran as white solid (2.3 g; 10 mmol); m.p. 114°–116° C. By proceeding analogously the following compounds were obtained:

6-cyano-1,2-dimethoxy-6H-dibenzo[b,d]thiopyran;
2-methyl-6-cyano-6H-dibenzo[b,d]thiopyran, and
2-chloro-6-cyano-6H-dibenzo[b,d]thiopyran.

EXAMPLE 5

To a stirred solution of 6-cyano-6H-dibenzo[b,d]thiopyran (4.5 g; 0.02 mol) and $CH_3I$ (28.4 g; 0.2 mol) in 100 ml of dimethylformamide, 50% NaH (1.5 g; 0.03 mol) was added in small portions. After 16 hours at room temperature the mixture was poured into water and extracted with diethyl ether. The organic phase was washed with water and dried over $Na_2SO_4$. Evaporation of the solvent gave 6-cyano-6-methyl-6H-dibenzo[b,d]thiopyran (3.58 g; 0.015 mol; yield 75%).

EXAMPLE 6

6-cyano-6H-dibenzo[b,d]thiopyran (2.5 g; 0.011 mol) was dissolved in 1 M methanolic KOH (46 ml) and the solution refluxed for 16 hours. After evaporation of the solvent the residue was dissolved in water and the solution washed with diethyl ether. The aqueous solution was then acidified with 23% HCl and extracted with ethyl acetate. The 6H-dibenzo[b,d]thiopyran-6-carboxylic acid was obtained by removal of the solvent; (1.8 g; 66%); m.p. 156°–159° C. By proceeding analogously the following compounds were obtained:

6-methyl-6H-dibenzo[b,d]thiopyran-6-carboxylic acid;
1,2-dimethoxy-6H-dibenzo[b,d]thiopyran-6-carboxylic acid;
2-chloro-6H-dibenzo[b,d]thiopyran-6-carboxylic acid; and
2-methyl-6H-dibenzo[b,d]thiopyran-6-carboxylic acid.

EXAMPLE 7

6-cyano-6H-dibenzo-[b,d]thiopyran (4 g; 0.018 mol) in 85% $H_2SO_4$ (30 ml) was heated at 80° C. for 3 hours. The solution was cooled and poured into 300 g of crushed ice. The precipitated 6H-dibenzo[b,d]thiopyran-6-carboxamide was filtered (3.3 g; yield 76%). By proceeding analogously the following compounds were obtained:

2-chloro-6H-dibenzo[b,d]thiopyran-6-carboxamide;
6-methyl-6H-dibenzo[b,d]thiopyran-6-carboxamide;
2-methyl-6H-dibenzo[b,d]thiopyran-6-carboxamide, and
1,2-dimethoxy-6H-dibenzo[b,d]thiopyran-6-carboxamide.

EXAMPLE 8

6H,6-cyano-dibenzo-[b,d]thiopyran (3.3 g; 0.015 mol) was added to a solution of 85% $H_2SO_4$ (1 ml) and methanol (1.5 ml). After heating at reflux temperature for 6 hours, the solution was poured into 50 ml of water and extracted with chloroform. The extracts were washed with water, dried over sodium sulfate and concentrated. The obtained 6H-dibenzo[b,d]thiopyran6-carboxylic acid methyl ester was treated with n.pentane and filtered; (2.6 g; yield 67%); m.p. 36°–46° C. Analogously by using the suitable alkyl alcohol, the following compounds were obtained:

6-methyl-6H-dibenzo[b,d]thiopyran-6-carboxylic acid, ethyl ester;
6H-dibenzo[b,d]thiopyran-6-carboxylic acid, ethyl ester;
2-chloro-6H-dibenzo[b,d]thiopyran-6-carboxylic acid, ethyl ester, and
2-methyl-6H-dibenzo[b,d]thiopyran-6-carboxylic acid, ethyl ester.

EXAMPLE 9

6H-dibenzo[b,d]thiopyran-6-carboxylic acid (4.8 g; 0.02 mol) was suspended in thionyl chloride (50 ml) and kept at room temperature overnight. The solution was evaporated in vacuo. The crude residue was dissolved in 100 ml of anhydrous dichloromethane and the obtained solution was added dropwise at 0/5° C. to a solution of morpholine (4.4 ml; 0.05 mol) in 100 ml of dichloromethane. After one hour the solution was washed with water, dried over sodium sulfate and concentrated. The obtained 6-morpholinocarbonyl-6H-dibenzo[b,d]thiopyran was crystallized from ethanol; (5.7 g; yield 92%). By proceeding analogously and using the suitable amine the following compounds were obtained:

6H-dibenzo[b,d]thiopyran-6-N-methyl-carboxamide;
6-(pyrrolidin-1-yl)carbonyl-6H-dibenzo[b,d]thiopyran;
6-(4-methyl-piperazin-1-yl)carbonyl-6H-dibenzo[b,d]thiopyran; and
6-[4-(2-pyridyl)-piperazin-1-yl]carbonyl-6H-dibenzo[b,d]thiopyran.

EXAMPLE 10

6H-dibenzo[b,d]thiopyran-6-carboxylic acid (3.4 g; 0.014 mol) was suspended in thionyl chloride (30 ml) and after 20 hours at room temperature the solution was evaporated in vacuo. The crude residue was dissolved in 80 ml of benzene and the obtained solution was added dropwise, at room temperature, to a solution of 2-dimethylaminoethanol (42 ml; 0.042 mol) in 80 ml of benzene. After half an hour the solution was washed with water and dried over sodium sulfate and concentrated to dryness. 6H-dibenzo[b,d]thiopyran-6-carboxylic acid, 2-dimethylamino-ethyl ester was obtained as oil; (3.0 g; yield 70%); NMR (CDCl$_3$) δ ppm: 2.12 (s) (6H,CH$_3$), 2.37 (t) (2H, —CH$_2$NMe$_2$), 4.07 (t) (2H, COOCH$_2$), 4.59 (s) (1H,C-6 proton), 7.1–7.5 (m) (6H; C-2, C-3, C-4, C-7, C-8 and C-9 phenyl protons), 7.78 (m) (2H; C-1 and C-10 phenyl protons). By proceeding analogously the following compounds were obtained:

6H-dibenzo[b,d]thiopyran-6-carboxylic acid, 3-dimethylaminopropyl ester;
6H-dibenzo[b,d]thiopyran-6-carboxylic acid, 2-diethylaminoethyl ester;
6H-dibenzo[b,d]thiopyran-6-carboxylic acid, 2-morpholinoethyl ester;
6H-dibenzo[b,d]thiopyran-6-carboxylic acid, 2-(pyrrolidin-1-yl)-ethyl ester;
6H-dibenzo[b,d]thiopyran-6-carboxylic acid, 2-(4-methylpiperazin-1-yl)-ethyl ester;
6H-dibenzo[b,d]thiopyran-6-carboxylic acid, 2-dimethylamino-ethylthio ester;
6-methyl-6H-dibenzo[b,d]thiopyran-6-carboxylic acid, 2-dimethylamino-ethyl ester;
1,2-dimethoxy-6H-dibenzo[b,d[thiopyran-6-carboxylic acid, 2-dimethylamino-ethyl ester;
2-chloro-6H-dibenzo[b,d]thiopyran-6-carboxylic acid, 2-dimethylamino-ethyl ester;
2-methyl-6H-dibenzo[b,d]thiopyran-6-carboxylic acid, 2-dimethylamino-ethyl ester;
6-methyl-6H-dibenzo[b,d]thiopyran-6-carboxylic acid, 2-diethylamino-ethyl ester;
1,2-dimethoxy-6H-dibenzo[b,d]thiopyran-6-carboxylic acid, 2-diethylamino-ethyl ester;
2-chloro-6H-dibenzo[b,d]thiopyran-6-carboxylic acid, 2-diethylamino-ethyl ester, and
2-methyl-6H-dibenzo-[b,d]thiopyran-6-carboxylic acid, 2-diethylamino-ethyl ester.

EXAMPLE 11

6H-dibenzo[b,d]thiopyran-6-carboxylic acid (1.7 g; 0.007 mol) was suspended in thionyl chloride (17 ml) and kept at room temperature for 20 hours. The solution was evaporated in vacuo. The crude residue was dissolved in 30 ml of benzene and the obtained solution was added dropwise, at room temperature, to a solution of N,N,N'-trimethylethylidenediamine (2.7 ml; 0.021 mol) in 30 ml of benzene. After half an hour the solution was thoroughly washed with water, dried over sodium sulfate and evaporated to dryness to obtain 6H-dibenzo[b,d]thiopyran-6-[N-(2-dimethylaminoethyl)-N-methyl]-carboxamide (1.5 g; yield 65%), oil. Analogously the following compounds were obtained:

6H-dibenzo[b,d]thiopyran-6-N-(2-dimethylaminoethyl)-carboxamide, and
6H-dibenzo[b,d]thiopyran-6-N-(3-dimethylaminopropyl)-carboxamide.

EXAMPLE 12

To an ethanolic solution ( 5 ml) of 6H-dibenzo[b,d]thiopyran-6-carboxylic acid, 2-dimethylamino-ethyl ester (1.56 g; 0.005 mol) 1M ethanolic HCl (5 ml) and diethyl ether (150 ml) were added.

The precipitate was filtered to give 6H-dibenzo[b,d]thiopyran-6-carboxylic acid, 2-dimethylamino-ethyl ester hydrochloride (1.65 g; yield 94%); m.p. 143°–153° C. dec. Analogously the following compounds were obtained:

6H-dibenzo[b,d]thiopyran-6-carboxylic acid, 2-diethylamino-ethyl ester, hydrochloride;
6H-dibenzo[b,d]thiopyran-6-carboxylic acid, 3-dimethylamino-propyl ester, hydrochloride;
6H-dibenzo[b,d]thiopyran-6-carboxylic acid, 2-dimethylamino-ethylthio ester, hydrochloride;
6H-dibenzo[b,d]thiopyran-6-carboxylic acid, 2-morpholinoethyl ester, hydrochloride;
6H-dibenzo[b,d]thiopyran-6-carboxylic acid, 2-(pyrrolidin-1-yl)-ethyl ester, hydrochloride;
6H-dibenzo[b,d]thiopyran-6-carboxylic acid, 2-(4-methyl-piperazin-1-yl)-ethyl ester, hydrochloride;
6-methyl-6H-dibenzo[b,d]thiopyran-6-carboxylic acid, 2-dimethylamino-ethyl ester, hydrochloride;
1,2-dimethoxy-6H-dibenzo[b,d]thiopyran-6-carboxylic acid, 2-dimethylamino-ethyl ester, hydrochloride;
2-chloro-6H-dibenzo[b,d]thiopyran-6-carboxylic acid, 2-dimethylamino-ethyl ester, hydrochloride;
2-methyl-6H-dibenzo[b,d]thiopyran-6-carboxylic acid, 2-dimethylamino-ethyl ester, hydrochloride;
6-methyl-6H-dibenzo[b,d]thiopyran-6-carboxylic acid, 2 -diethylamino-ethyl ester, hydrochloride;
1,2-dimethoxy-6H-dibenzo[b,d]thiopyran-6-carboxylic acid, 2-diethylamino-ethyl ester, hydrochloride;
2-chloro-6H-dibenzo[b,d]thiopyran-6-carboxylic acid, 2-diethylamino-ethyl ester, hydrochloride, and
2-methyl-6H-dibenzo[b,d]thiopyran-6-carboxylic acid, 2-diethylamino-ethyl ester, hydrochloride.

EXAMPLE 13

6H-dibenzo[b,d]thiopyran-6-carboxylic acid (1.9 g; 0.008 mol) was dissolved in 0.5 N ethanolic NaOH (16 ml). The solution was diluted with acetone. The obtained 6H-dibenzo[b,d]thiopyran-6-carboxylic acid sodium salt was filtered (1.9 g; yield 90%); m.p. 240° C. dec. Analogously the following compounds were obtained:

6-methyl-6H-dibenzo[b,d]thiopyran-6-carboxylic acid sodium salt;

1,2-dimethoxy-6H-dibenzo[b,d]thiopyran-6-carboxylic acid sodium salt;

2-chloro-6H-dibenzo[b,d]thiopyran-6-carboxylic acid sodium salt, and 2-methyl-6H-dibenzo[b,d]thiopyran-6-carboxylic acid sodium salt.

EXAMPLE 14

6H-dibenzo[b,d]thiopyran-6-carboxylic acid, methyl ester (4.1 g; 0.016 mol) was dissolved in N/5 methanolic KOH (50 ml) and the solution was heated at reflux for 4 hours. The solution was cooled and poured in diluted HCl and extracted with chloroform. The extracts were dried over $Na_2SO_4$ and concentrated. The residue was solidified in n.pentane to give 6H-dibenzo[b,d]thiopyran-6-carboxylic acid; (3 g; yield 77%); m.p. 156°–159° C.

EXAMPLE 15

To a solution of 6H-dibenzo[b,d]thiopyran-6-[N-(2-dimethylaminoethyl)-N-methyl]-carboxamide (1.16 g) in isopropyl ether (25 ml) the stoichiometric amount of gaseous HCl in isopropyl ether solution (50 ml) was added. The precipitate was filtered and washed with isopropyl ether to give 1.10 g (78%) of 6H-dibenzo[b,d]thiopyran-6-[N(2-dimethylaminoethyl)-N-methyl]-carboxamide hydrochloride, m.p. 160° dec. Analogously the following compounds were obtained:

6H-dibenzo[b,d]thiopyran-6-N-(2-dimethylaminoethyl)-carboxamide, hydrochloride; and 6H-dibenzo[b,d]thiopyran-6-N-(3-dimethylaminopropyl)-carboxamide, hydrochloride.

FORMULATION EXAMPLES

Formulation 1: Tablet (50 mg)

Tablets, each weighing 150 mg and containing 50 mg of the active substance were manufactured as follows:

| Composition (for 10000 tablets) | |
|---|---|
| 6H—dibenzo[b,d]thiopyran-6-carboxylic acid, 2-N,N—dimethylamino-ethyl ester | 500 g |
| Lactose | 710 g |
| Corn starch | 238 g |
| Talc powder | 36 g |
| Magnesium stearate | 16 g |

6H-dibenzo[b,d]thiopyran-6-carboxylic acid, 2-N,N-dimethylamino-ethyl ester, lactose and a half of the corn starch were mixed; the mixture was then forced through a sieve of 0.5 mm openings. Corn starch (18 g)was suspended in warm water (180 ml). the resulting paste was used to granulate the powder. The granules were dried, comminuted on a sieve of sieve size 1.4 mm, then the remaining quantity of starch, talc and magnesium stearate was added, carefully mixed, and processed into tablets using punches of 8 mm diameter.

Formulation 2: intramuscular injection

An injectable pharmaceutical composition was manufactured by dissolving 50–100 mg of 6H-dibenzo[b,d]-thiopyran-6-carboxylic aci, 2-N,N-dimethylamino-ethyl ester hydrochloride in sterile water or sterile normal saline solution (2–5 ml). Analogously, injectable pharmaceutical compositions containing the compounds previously described in the preceding examples were prepared.

| Formulation 3: Capsules (50 mg) | |
|---|---|
| 6H—dibenzo[b,d]thiopyran-6-carboxylic acid, 2-N,N—dimethylamino-ethyl ester | 50 |
| Lactose | 298 |
| Corn starch | 50 |
| Magnesium stearate | 2 |
| Total | 400 mg |

Encapsulate in two-piece hard gelatin capsules.

We claim:

1. A compound of general formula (I)

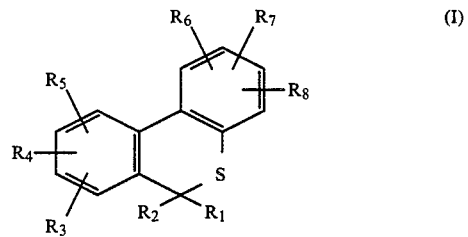

wherein $R_1$ represents
(a) carboxy;
(b) esterified carboxy;
(c) a

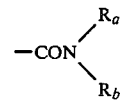

group, wherein each of $R_a$ and $R_b$, being the same or different, is hydrogen or $C_1$–$C_6$ alkyl, or $R_a$ and $R_b$, taken together with the nitrogen atom to which they are linked, form a saturated heteromonocyclic ring, optionally containing a further heteroatom chosen from oxygen, sulphur and nitrogen, wherein the additional nitrogen atom may be unsubstituted or substituted by $C_1$–$C_6$ alkyl, pyridyl or by phenyl; or (d) a

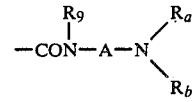

group, wherein $R_9$ is hydrogen or $C_1$–$C_6$ alkyl, A is a $C_2$–$C_6$ alkylene chain and $R_a$ and $R_b$ are as defined above;

$R_2$ represents hydrogen or $C_1$–$C_6$ alkyl;

each of $R_3$, $R_4$, $R_5$, $R_6$, $R_7$ and $R_8$, which may be the same or different, is hydrogen, halogen, $C_1$–$C_6$ alkyl, $C_3$–$C_4$-alkenyloxy or $C_1$–$C_6$ alkoxy; and the pharmaceutically acceptable salts thereof.

2. A compound of formula (I) according to claim 1 wherein $R_1$ represents (a') an esterified carboxy group of formula —COXR'$_{10}$, wherein X is —O— or —S— and R'$_{10}$ is $C_1$–$C_4$ alkyl unsubstituted or substituted by a

group, wherein each of $R'_a$ and $R'_b$ is independently hydrogen or $C_1$-$C_4$ alkyl, or $R'_a$ and $R'_b$ taken together with the nitrogen atom to which they are linked, form a pyrrolidine, piperidine, morpholine, thiomorpholine or piperazine ring, wherein the piperazine ring may be unsubstituted or substituted by $C_1$-$C_4$ alkyl, pyridyl or by phenyl; or (b') a

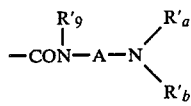

group, wherein $R'_9$ is hydrogen or $C_1$-$C_4$ alkyl, A is as defined in claim 1 and $R'_a$ and $R'_b$ are as defined above;

$R_2$ is hydrogen or $C_1$-$C_4$ alkyl;

each of $R_3$, $R_4$, $R_5$, $R_6$, $R_7$ and $R_8$ is independently hydrogen, chlorine, bromine, $C_1$-$C_4$ alkyl or $C_1$-$C_4$ alkoxy; and the pharmaceutically acceptable salts thereof.

3. A compound of formula (I) according to claim 1 wherein

R represents (a'') a $C_1$-$C_4$ alkoxy-carbonyl group;

(b'')

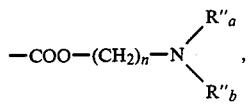

wherein n is 2 or 3, each of $R''_a$ and $R''_b$ is independently $C_1$-$C_4$ alkyl or $R''_a$ and $R''_b$ taken together with the nitrogen atom to which they are linked form a pyrrolidine, morpholine or piperidine ring;

(c'')

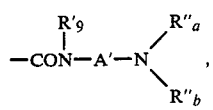

wherein $R'_9$ is hydrogen or $C_1$-$C_4$-alkyl, A' is a $C_2$-$C_4$ alkenylene chain and $R''_a$ and $R''_b$ are as defined above;

$R_2$ is hydrogen;

each of $R_3$, $R_4$, $R_5$, $R_6$, $R_7$ and $R_8$ is independently hydrogen, chlorine, $C_1$-$C_4$ alkyl or $C_1$-$C_4$ alkoxy; and the pharmaceutically acceptable salts thereof.

4. A compound of formula (I) according to claim 1 wherein $R_1$ is (a''') $C_1$-$C_4$ alkoxy-carbonyl;

(b''')

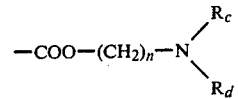

wherein n is 2 or 3 and each of $R_c$ and $R_d$ is independently $C_1$-$C_4$ alkyl; or (c''')

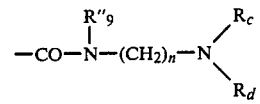

wherein $R''_9$ is $C_1$-$C_4$ alkyl and $R_c$, $R_d$ and n are as defined above;

$R_2$ is hydrogen;

each of $R_3$, $R_4$, $R_5$, $R_6$, $R_7$ and $R_8$ is hydrogen; and the pharmaceutically acceptable salts thereof.

5. 6H-dibenzo[b,d]thiopyran-6-carboxylic acid, 2-N,N--dimethylamino-ethyl ester and the pharmaceutically acceptable salts thereof.

6. A compound selected from the group consisting of:
6H-dibenzo[b,d]thiopyran-6-carboxylic acid;
6H-dibenzo[b,d]thiopyran-6-carboxylic acid, 2-N,N-dimethylamino-ethylthio ester;
6H-dibenzo[b,d]thiopyran-6-carboxylic acid, 3-N,N-dimethylamino-propyl ester;
6H-dibenzo[b,d]thiopyran-6-carboxylic acid, 2-N,N-diethylamino-ethyl ester;
6H-dibenzo[b,d]thiopyran-6-carboxylic acid, 2-morpholinoethyl ester;
6H-dibenzo[b,d]thiopyran-6-carboxylic acid, 2-(pyrrolidin-1-yl)-ethyl ester;
6H-dibenzo[b,d]thiopyran-6-N-(2-N,N-dimethylamino-ethyl)carboxamide;
6H-dibenzo[b,d]thiopyran-6-N-methyl-N-(2-N,N-dimethylaminoethyl)-carboxamide;
6H-dibenzo[b,d]thiopyran-6-N-(3-N,N-dimethylamino-propyl)carboxamide;
6-(4-methyl-piperazin-1-yl)-carbonyl-6H-dibenzo[b,d]thiopyran;
6-[4-(2-pyridyl)-piperazin-1-yl]-carbonyl-6H-dibenzo[b,d]thiopyran; and the pharmaceutically acceptable salts thereof.

7. A pharmaceutical composition containing a suitable carrier and/or diluent and, as an active principle, a compound of formula (I) according to claim 1, or a pharmaceutically acceptable salt thereof.

8. A method of treating transplant reaction in a patient arising from transplant of kidneys, heart, bone marrow, skin and/or endocrine glands, said method comprising administering to said patient an effective amount of a compound of claim 1.

9. A method of treating autoimmune disorders arising from rheumatoid arthritis, systemic lupus erythematosus, glomerulonephritis, vasculitis or blood dyscrasias, said method comprising administering to said patient an autoimmune effective amount of a compound of claim 1.

10. A method of treating bacterial and viral infections in a patient in need of such treatment, said method comprising administering to said patient an effective amount of a compound of claim 1.

* * * * *